US010989126B2

United States Patent
Surnilla et al.

(10) Patent No.: US 10,989,126 B2
(45) Date of Patent: Apr. 27, 2021

(54) METHODS AND SYSTEM FOR OPERATING AN OXYGEN SENSOR

(71) Applicant: Ford Global Technologies, LLC, Dearborn, MI (US)

(72) Inventors: Gopichandra Surnilla, West Bloomfield, MI (US); Hao Zhang, Ann Arbor, MI (US); Christopher Paul Glugla, Macomb, MI (US); Jacobus Hendrik Visser, Farmington Hills, MI (US); Richard E. Soltis, Saline, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 0 days.

(21) Appl. No.: 16/275,223

(22) Filed: Feb. 13, 2019

(65) Prior Publication Data
US 2020/0256268 A1    Aug. 13, 2020

(51) Int. Cl.
| | | |
|---|---|---|
| F02D 41/02 | (2006.01) | |
| F02D 35/00 | (2006.01) | |
| G01N 33/00 | (2006.01) | |
| F02D 41/14 | (2006.01) | |
| G01M 15/10 | (2006.01) | |
| F02D 41/06 | (2006.01) | |

(52) U.S. Cl.
CPC ..... *F02D 41/0235* (2013.01); *F02D 35/0023* (2013.01); *F02D 35/0046* (2013.01); *F02D 41/064* (2013.01); *F02D 41/1491* (2013.01); *G01M 15/104* (2013.01); *G01N 33/0008* (2013.01)

(58) Field of Classification Search
CPC .. F02D 41/02; F02D 41/0235; F02D 35/0023; F02D 35/0046; F02D 41/064; F02D 41/1491; G01M 15/104; G01N 33/0008
See application file for complete search history.

(56) References Cited

U.S. PATENT DOCUMENTS

| | | |
|---|---|---|
| 5,111,792 A | 5/1992 | Nagai et al. |
| 5,719,778 A | 2/1998 | Suzumura et al. |
| 5,974,857 A | 11/1999 | Yamashita et al. |
| 9,528,448 B2 * | 12/2016 | Makled ................ F02D 19/088 |
| 2005/0241361 A1 * | 11/2005 | Smith ................ G01N 27/4067 73/1.06 |

OTHER PUBLICATIONS

Glugla, C. et al., "Systems and Methods for Oxygen Sensor Light-Off," U.S. Appl. No. 16/223,948, filed Dec. 18, 2018, 47 pages.

* cited by examiner

*Primary Examiner* — Hieu T Vo
(74) *Attorney, Agent, or Firm* — Geoffrey Brumbaugh; McCoy Russell LLP

(57) ABSTRACT

Systems and methods for operating an internal combustion engine that includes an oxygen sensor are described. In one example, a voltage that is applied to a heating element of an oxygen sensor is integrated to determine a resistance of the heating element. The resistance of the heating element is the basis for adjusting voltage applied to the heating element during subsequent engine starts.

20 Claims, 4 Drawing Sheets

METHODS AND SYSTEM FOR OPERATING AN OXYGEN SENSOR

FIELD

The present description relates to methods and a system for operating an oxygen sensor that is coupled to an internal combustion engine.

BACKGROUND AND SUMMARY

An oxygen sensor may be coupled to an exhaust system of an internal combustion engine. The oxygen sensor may provide feedback that may be applied to adjust the engine's air-fuel ratio. During engine cold starting, it may be useful to operate the engine in closed-loop fuel control because operating the engine too rich may increase hydrocarbon emissions and operating the engine too lean may result in engine misfire. Nevertheless, the oxygen sensor may not output an indication of the engine's air-fuel ratio until the oxygen sensor reaches a threshold temperature that may take more than tens of seconds to achieve. Consequently, the engine may be operated in an open loop air-fuel ratio control mode while output of the oxygen sensor does not accurately indicate the engine's air-fuel ratio. The engine may be operated with a rich air-fuel ratio while operating in open loop air-fuel control mode so that the engine does not stall or misfire. However, operating the engine rich may significantly increase the engine's hydrocarbon emissions.

The inventors herein have recognized the above-mentioned issues and have developed an oxygen sensor operating method, comprising: supplying a voltage to an oxygen sensor heater during a cold engine start via a controller; integrating the voltage; and adjusting the voltage applied to the oxygen sensor heater applied during a subsequent cold engine start via the controller responsive to the integrated voltage.

By integrating a voltage that is applied to an oxygen sensor during an engine cold start, it may be possible to provide the technical result of being able to enter closed loop air-fuel ratio control sooner so that engine hydrocarbon emissions may be reduced while the possibility of engine stalling may be reduced. In particular, a resistance of an oxygen sensor heater may be estimated so that a higher level of electrical power may be supplied to the oxygen sensor heater, thereby increasing the oxygen temperature to a level where the oxygen sensor's pumping cell begins to provide a meaningful indication of engine air-fuel ratio. Further, by knowing the oxygen sensor's resistance, the amount of power delivered to the oxygen sensor during the cold engine start may be regulated to a level where the possibility of oxygen sensor degradation may be reduced.

The present description may provide several advantages. Specifically, the approach may improve engine starting robustness. In addition, the approach may reduce engine emissions. Further, the approach may reduce the possibility of oxygen sensor degradation during cold engine starting. Further still, the approach may be realized at no or little expense as compared to present engine control systems.

The above advantages and other advantages, and features of the present description will be readily apparent from the following Detailed Description when taken alone or in connection with the accompanying drawings.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The advantages described herein will be more fully understood by reading an example of an embodiment, referred to herein as the Detailed Description, when taken alone or with reference to the drawings, where.

DETAILED DESCRIPTION

Figure 2:
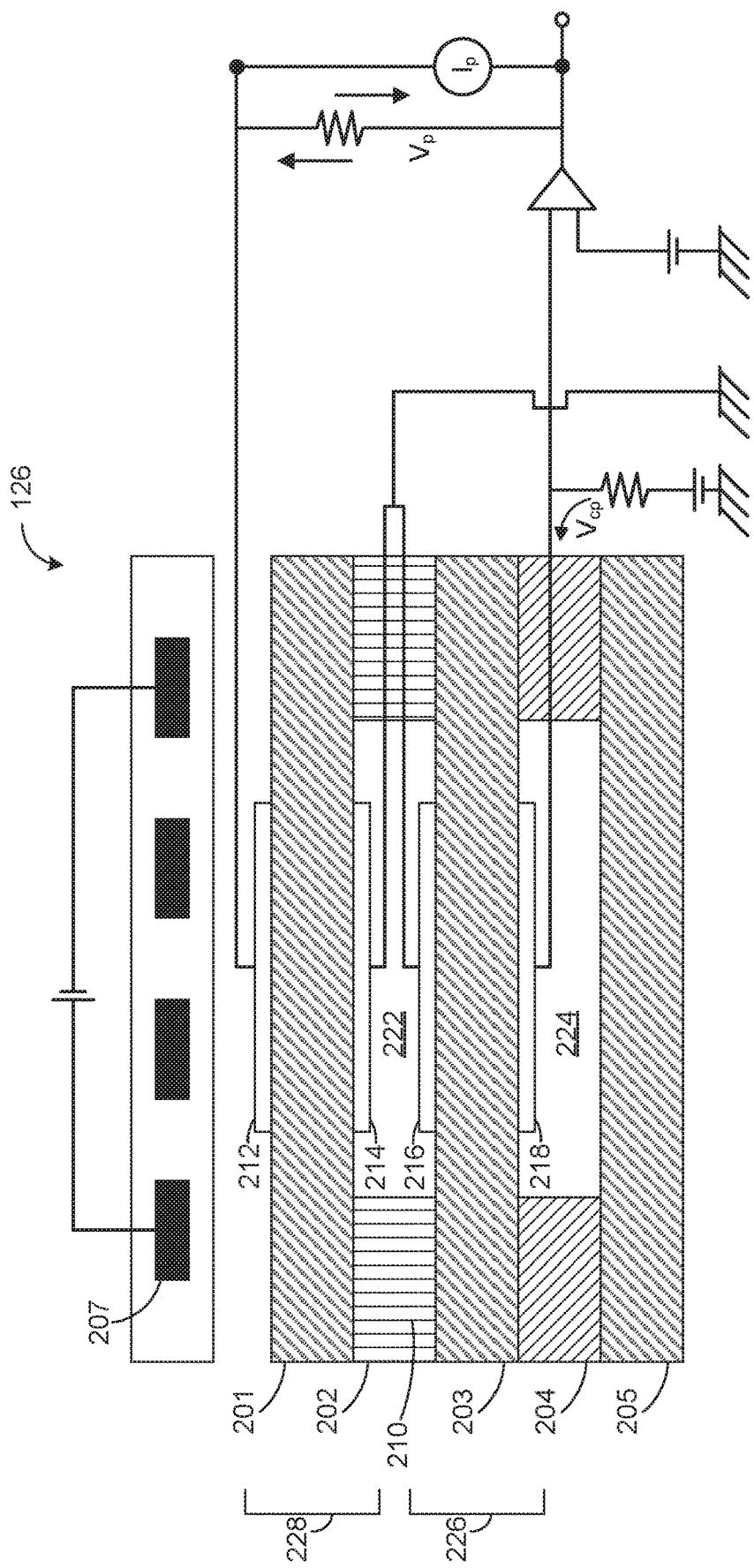
FIG. 2 is a schematic diagram of an oxygen sensor.
Figure 3:
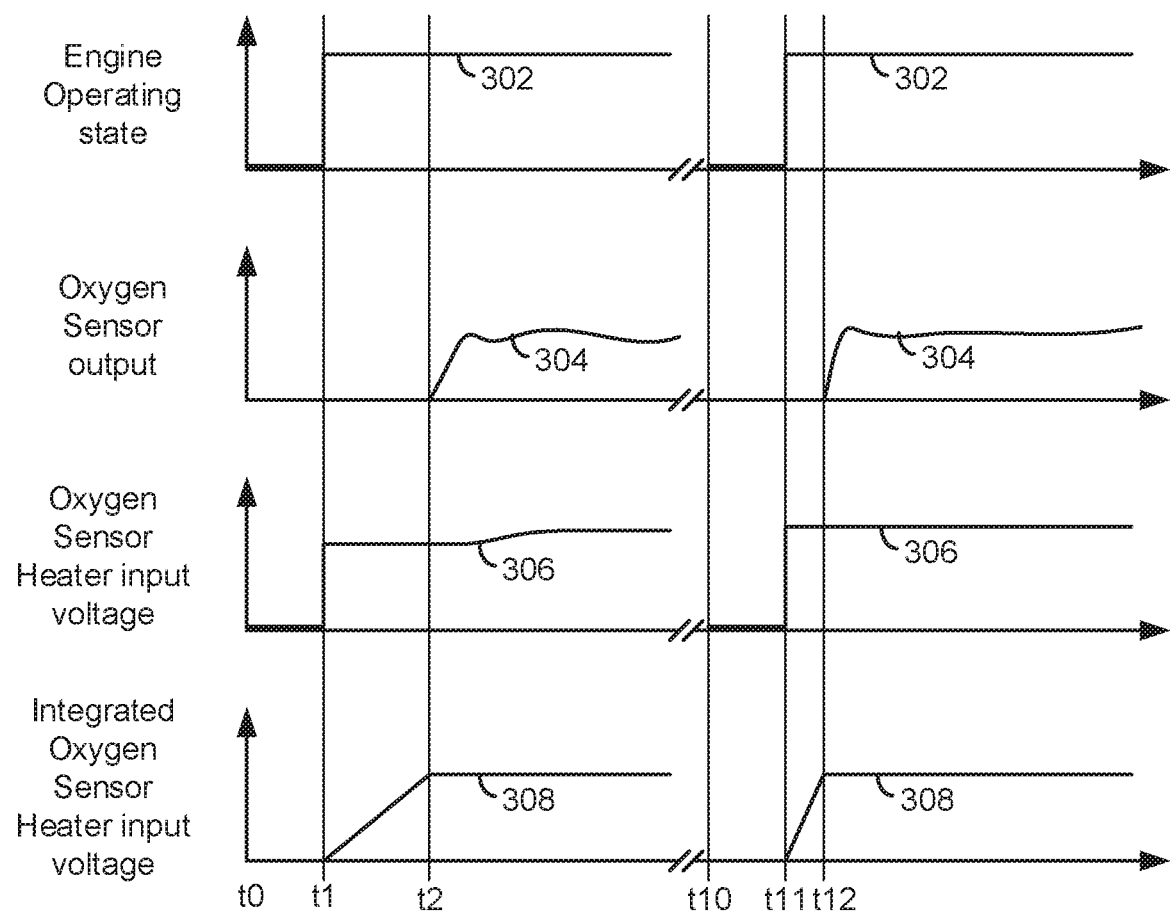
FIG. 3 shows plots of an engine operating sequence according to the method of FIG. 4.
Figure 4:
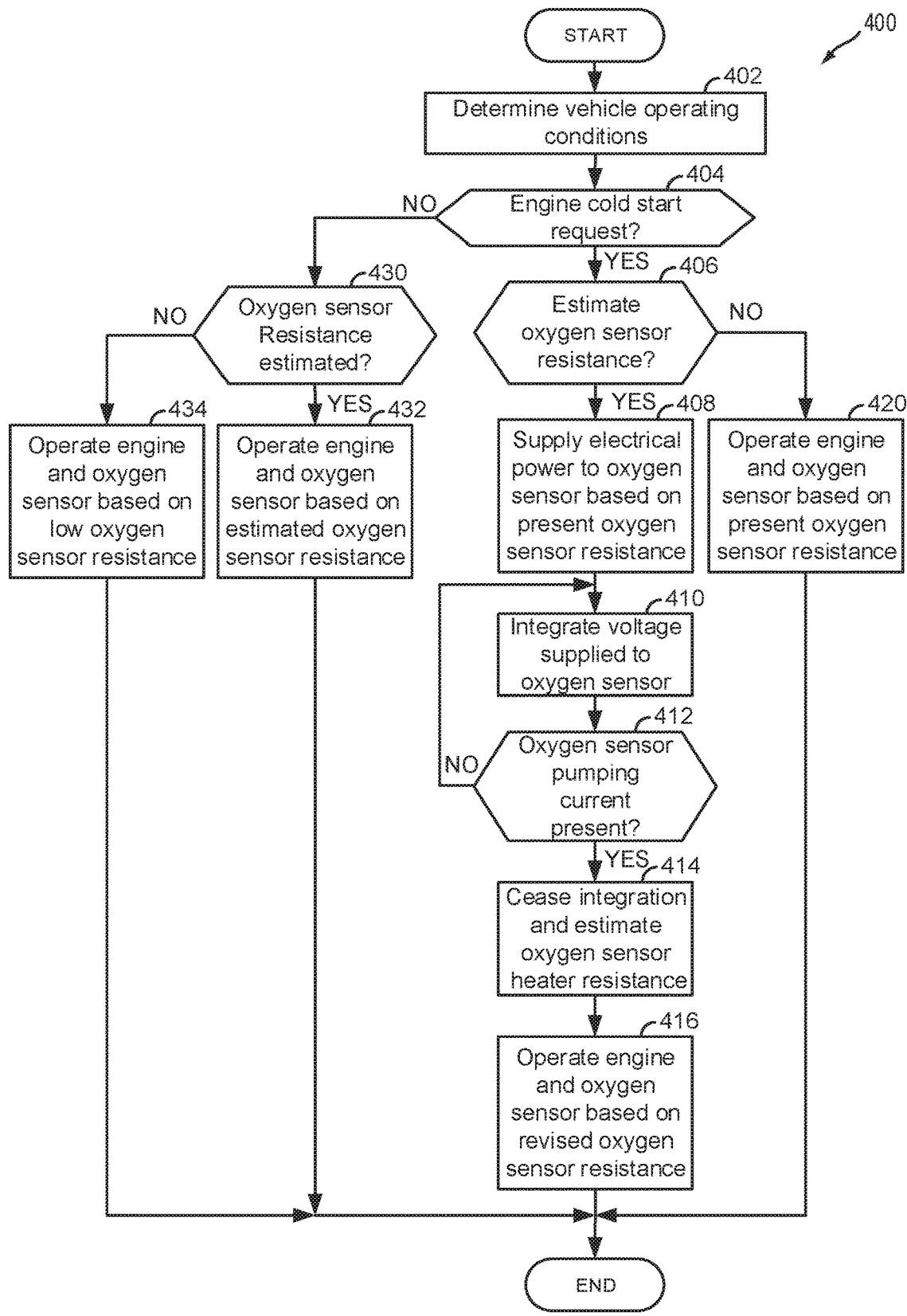
FIG. 4 shows a method for operating an engine and controlling an oxygen sensor.

The present description is related to improving engine cold starting and reducing engine emissions via achieving meaningful output from an oxygen sensor sooner after an engine is started. In one example, a voltage that is applied to an oxygen sensor is adjusted responsive to an estimated resistance of the oxygen sensor so that sufficient electrical power may be provided to the oxygen sensor without causing degradation of the oxygen sensor. The engine may be of the type shown in FIG. 1. The oxygen sensor may include a heating element as shown in FIG. 2. An engine operating sequence that illustrates the method of FIG. 4 is shown in FIG. 3. An engine and oxygen sensor may be operated according to the method of FIG. 4.

Figure 1:
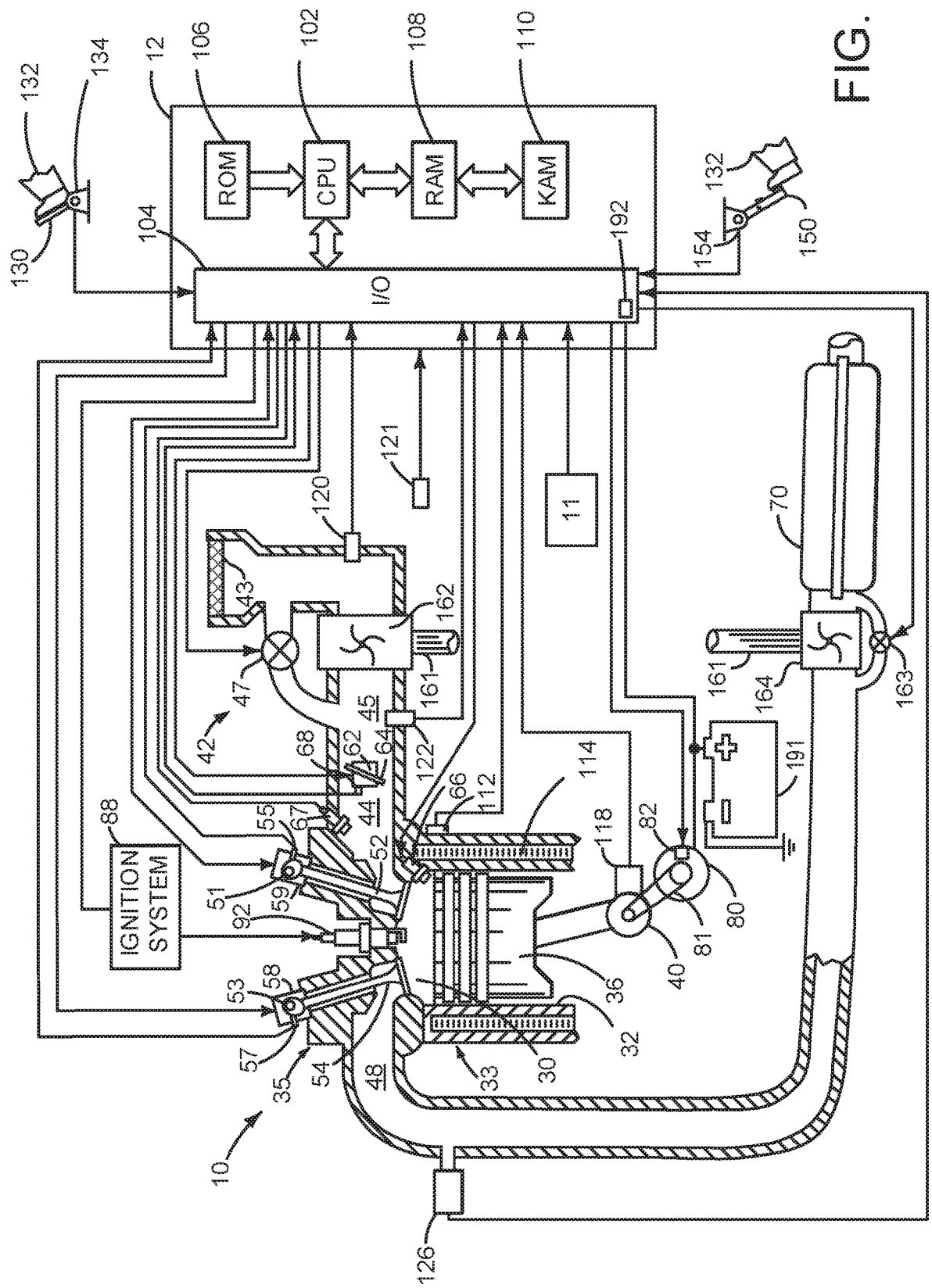
FIG. 1 is a schematic diagram of an engine.

Referring to FIG. 1, internal combustion engine 10, comprising a plurality of cylinders, one cylinder of which is shown in FIG. 1, is controlled by electronic engine controller 12. The controller 12 receives signals from the various sensors shown in FIGS. 1 and 2 and employs the actuators shown in FIGS. 1 and 2 to adjust engine operation based on the received signals and instructions stored in memory of controller 12.

Engine 10 is comprised of cylinder head 35 and block 33, which include combustion chamber 30 and cylinder walls 32. Piston 36 is positioned therein and it reciprocates via a connection to crankshaft 40. Combustion chamber 30 is shown communicating with intake manifold 44 and exhaust manifold 48 via respective intake valve 52 and exhaust valve 54. Each intake and exhaust valve may be operated by an intake cam 51 and an exhaust cam 53. The position of intake cam 51 may be determined by intake cam sensor 55. The position of exhaust cam 53 may be determined by exhaust cam sensor 57. Timing of intake valve 52 may be adjusted relative to crankshaft 40 via cam phasing device 59. Timing of exhaust valve 54 may be adjusted relative to crankshaft 40 via cam phasing device 58.

Direct fuel injector 66 is shown positioned to inject fuel directly into cylinder 30, which is known to those skilled in the art as direct injection. Port fuel injector 67 is shown positioned to inject fuel into the intake port of cylinder 30, which is known to those skilled in the art as port injection. Fuel injectors 66 and 67 deliver liquid fuel in proportion to pulse widths provided by controller 12. Fuel is delivered to fuel injectors 66 and 67 by a fuel system (not shown) including a fuel tank, fuel pump, and fuel rail.

In addition, intake manifold 44 is shown communicating with turbocharger compressor 162 and engine air intake 42.

In other examples, compressor 162 may be a supercharger compressor. Shaft 161 mechanically couples turbocharger turbine 164 to turbocharger compressor 162. Optional electronic throttle 62 adjusts a position of throttle plate 64 to control air flow from compressor 162 to intake manifold 44. Pressure in boost chamber 45 may be referred to a throttle inlet pressure since the inlet of throttle 62 is within boost chamber 45. The throttle outlet is in intake manifold 44. In some examples, throttle 62 and throttle plate 64 may be positioned between intake valve 52 and intake manifold 44 such that throttle 62 is a port throttle. Compressor recirculation valve 47 may be selectively adjusted to a plurality of positions between fully open and fully closed. Waste gate 163 may be adjusted via controller 12 to allow exhaust gases to selectively bypass turbine 164 to control the speed of compressor 162. Air filter 43 cleans air entering engine air intake 42.

Distributorless ignition system 88 provides an ignition spark to combustion chamber 30 via spark plug 92 in response to controller 12. Universal Exhaust Gas Oxygen (UEGO) sensor 126 is shown coupled to exhaust manifold 48 upstream of three-way catalyst 70. Alternatively, a two-state exhaust gas oxygen sensor may be substituted for UEGO sensor 126.

Catalyst 70 can include multiple bricks and a three-way catalyst coating, in one example. In another example, multiple emission control devices, each with multiple bricks, can be used.

Alternator 80 is shown mechanically coupled to crankshaft 40 via belt 81. Alternator may convert torque from engine 10 into electrical charge, and the electric charge may be directed to electric energy storage device (e.g., battery) 191. Controller 12 may adjust a voltage output via alternator 80 via adjusting an amount of electric current that is supplied to alternator field coil 82. The voltage that is supplied to electric energy storage device 191 may also be directed to power oxygen sensor 126, including an oxygen sensor heater shown in FIG. 2. The voltage supplied to oxygen sensor 126 may be selectively controlled via controller 12. Alternatively, controller 12 may include a buck/boost voltage regulator 192 to increase or decrease a voltage at electric energy storage device 191 to regulate an amount of electric power that may be supplied to oxygen sensor 126.

Controller 12 is shown in FIG. 1 as a conventional microcomputer including: microprocessor unit 102, input/output ports 104, read-only memory 106 (e.g., non-transitory memory), random access memory 108, keep alive memory 110, and a conventional data bus. Controller 12 is shown receiving various signals from sensors coupled to engine 10, in addition to those signals previously discussed, including: engine coolant temperature (ECT) from temperature sensor 112 coupled to cooling sleeve 114; a position sensor 134 coupled to an accelerator pedal 130 (e.g., a human/machine interface) for sensing force applied by human driver 132; a position sensor 154 coupled to brake pedal 150 (e.g., a human/machine interface) for sensing force applied by human driver 132, a measurement of engine manifold pressure (MAP) from pressure sensor 122 coupled to intake manifold 44; barometric pressure from barometric pressure sensor 121; an engine position sensor from a Hall effect sensor 118 sensing crankshaft 40 position; a measurement of air mass entering the engine from sensor 120; and a measurement of throttle position from sensor 68. Barometric pressure may also be sensed (sensor not shown) for processing by controller 12. In a preferred aspect of the present description, engine position sensor 118 produces a predetermined number of equally spaced pulses every revolution of the crankshaft from which engine speed (RPM) can be determined.

Controller 12 may also receive input from human/machine interface 11. A request to start the engine or vehicle may be generated via a human and input to the human/machine interface 11. The human/machine interface 11 may be a touch screen display, pushbutton, key switch or other known input/output device.

During operation, each cylinder within engine 10 typically undergoes a four stroke cycle: the cycle includes the intake stroke, compression stroke, expansion stroke, and exhaust stroke. During the intake stroke, generally, the exhaust valve 54 closes and intake valve 52 opens. Air is introduced into combustion chamber 30 via intake manifold 44, and piston 36 moves to the bottom of the cylinder so as to increase the volume within combustion chamber 30. The position at which piston 36 is near the bottom of the cylinder and at the end of its stroke (e.g. when combustion chamber 30 is at its largest volume) is typically referred to by those of skill in the art as bottom dead center (BDC).

During the compression stroke, intake valve 52 and exhaust valve 54 are closed. Piston 36 moves toward the cylinder head so as to compress the air within combustion chamber 30. The point at which piston 36 is at the end of its stroke and closest to the cylinder head (e.g. when combustion chamber 30 is at its smallest volume) is typically referred to by those of skill in the art as top dead center (TDC). In a process hereinafter referred to as injection, fuel is introduced into the combustion chamber. In a process hereinafter referred to as ignition, the injected fuel is ignited by known ignition means such as spark plug 92, resulting in combustion.

During the expansion stroke, the expanding gases push piston 36 back to BDC. Crankshaft 40 converts piston movement into a rotational power of the rotary shaft. Finally, during the exhaust stroke, the exhaust valve 54 opens to release the combusted air-fuel mixture to exhaust manifold 48 and the piston returns to TDC. Note that the above is shown merely as an example, and that intake and exhaust valve opening and/or closing timings may vary, such as to provide positive or negative valve overlap, late intake valve closing, or various other examples.

FIG. 2 shows a schematic view of an example embodiment of an oxygen sensor 126 configured to measure a concentration of oxygen ($O_2$) in an exhaust gas stream in an exhaust passage. In some examples, the sensor 126 may be a UEGO (e.g., linear) sensor.

As shown in FIG. 2, the sensor 126 comprises a plurality of layers of one or more ceramic materials arranged in a stacked configuration. In the embodiment of FIG. 2, five ceramic layers are depicted as layers 201, 202, 203, 204, and 205. These layers include one or more layers of a solid electrolyte capable of conducting ionic oxygen. Examples of suitable solid electrolytes include, but are not limited to, zirconium oxide-based materials. Further, in some embodiments, a heater 207 may be disposed in thermal communication with the layers to increase the ionic conductivity of the layers. While the depicted oxygen sensor is formed from five ceramic layers, it will be appreciated that the oxygen sensor may include other suitable numbers of ceramic layers.

The layer 202 includes a material or materials creating a diffusion path 210. The diffusion path 210 is configured to introduce gasses into a first internal cavity 222 via diffusion. The diffusion path 210 may be configured to allow one or more components of intake air or exhaust gasses, including but not limited to a desired analyte (e.g., $O_2$), to diffuse into internal cavity 222 at a more limiting rate than the analyte can be pumped in or out by a pumping electrodes pair 212 and 214. In this manner, a stoichiometric level of $O_2$ may be obtained in the first internal cavity 222.

The sensor 126 further includes a second internal cavity 224 within the layer 204 separated from the first internal cavity 222 by the layer 203. The second internal cavity 224 is configured to maintain a constant oxygen partial pressure equivalent to a stoichiometric condition; e.g., an oxygen level present in the second internal cavity 224 is equal to that which the intake air or exhaust gas would have if the air-fuel ratio were stoichiometric. The oxygen concentration in the second internal cavity 224 is held constant by pumping voltage $V_{cp}$. Herein, the second internal cavity 224 may be referred to as a reference cell.

A pair of sensing electrodes 216 and 218 is disposed in communication with the first internal cavity 222 and the reference cell 224. The sensing electrodes pair 216 and 218 detects a concentration gradient that may develop between the first internal cavity 222 and the reference cell 224 due to an oxygen concentration in the intake air or exhaust gas that is higher than or lower than the stoichiometric level. A high oxygen concentration may be caused by a lean intake air or exhaust gas mixture, while a low oxygen concentration may be caused by a rich mixture. A pair of pumping electrodes 212 and 214 is disposed in communication with the internal cavity 222, and is configured to electrochemically pump a selected gas constituent (e.g., $O_2$) from internal cavity 222 through layer 201 and out of the sensor 126. Alternatively, the pair of pumping electrodes 212 and 214 may be configured to electrochemically pump a selected gas through layer 201 and into internal cavity 222. Herein, the pumping electrodes pair 212 and 214 may be referred to as an $O_2$ pumping cell.

The electrodes 212, 214, 216, and 218 may be made of various suitable materials. In some embodiments, the electrodes 212, 214, 216, and 218 may be at least partially made of a material that catalyzes the dissociation of molecular oxygen. Examples of such materials include, but are not limited to, electrodes containing platinum and/or silver.

The process of electrochemically pumping the oxygen out of or into the internal cavity 222 includes applying a voltage $V_p$ across the pumping electrode pair 212 and 214. The pumping voltage $V_p$ applied to the $O_2$ pumping cell pumps oxygen into or out of the first internal cavity 222 in order to maintain a stoichiometric level of oxygen in the cavity pumping cell. The resulting pumping current $I_p$ is proportional to the concentration of oxygen in the exhaust gas. A suitable control system (not shown in FIG. 2) generates the pumping current signal $I_p$ as a function of the intensity of the applied pumping voltage $V_p$ required to maintain a stoichiometric level within the first internal cavity 222. Thus, a lean mixture will cause oxygen to be pumped out of the internal cavity 222 and a rich mixture will cause oxygen to be pumped into the internal cavity 222.

It should be appreciated that the oxygen sensor described herein is merely an example embodiment of an oxygen sensor, and that other embodiments of oxygen sensors may have additional and/or alternative features and/or designs.

It is well known that the conductivity of a material changes with temperature. For an oxygen ionic conducting electrolyte such as zirconia, the ionic conductivity typically increases as the temperature increases. Other factors such as impurities, grain boundaries, structure, and geometry can affect the conductivity of the zirconia. For a fixed geometry and structure, the impedance (which is the inverse of the conductivity) of a zirconia element is directly related to the temperature of the element. Thus, the temperature of an oxygen sensor element may be determined by measuring the impedance of the oxygen sensor element. The oxygen sensor element impedance may be measured by measuring the voltage drop across the oxygen sensor element (e.g., by using an AC technique). For oxygen sensor 126, the sensor element impedance may be specifically measured across either sensing cell 226, which comprises layer 203 and electrodes 216 and 218, or pumping cell 228, which comprises layer 201 and electrodes 212 and 214, for example. In this approach, impedance measurement of a cell may be based on the applied voltage and resulting current associated with that cell—e.g., the impedance of pumping cell 228 may be determined based on the pumping voltage $V_p$ applied to the pumping cell and the resulting pumping current $I_p$. The impedance of sensing cell 226 may be analogously determined based on the pumping voltage applied to the sensing cell and the resulting pumping current. However, the approach for determining oxygen sensor heater resistance described in the method of FIG. 4 may be an improvement for estimating oxygen sensor resistance at low oxygen sensor temperatures because the oxygen sensor resistance may be very high.

In some approaches, the impedance of an oxygen sensor is used to control the temperature of the oxygen sensor. Since, as described above, the impedance of an oxygen sensor element can be used as an indication of the temperature of the sensor element, the impedance of the sensor element may be measured in real time and used to control its temperature—e.g., the output of a heater such as heater 207 may be controlled in closed loop fashion to minimize the difference between a desired sensor element impedance and an actual (e.g., measured) sensor element impedance, and thus to minimize the difference between a desired sensor temperature and an actual sensor temperature. In this way, the oxygen sensor may be adjusted to a desired sensor temperature by controlling a voltage that is applied to the heater, thereby controlling heater temperature according to heater impedance or resistance.

The heater resistance and sensor element impedance may be combined in various suitable manners to determine the temperature of oxygen sensor 126—e.g., a weighted average of the two quantities may be computed, with the sensor temperature determined based on the weighted average. In some examples, one or both of the heater resistance and sensor element impedance may be selected and potentially combined based on predetermined knowledge that one parameter is more accurate than the other in a range of temperatures. For example, oxygen sensor temperature may be preferentially determined based on heater resistance for a range of temperatures in which it is known that heater resistance temperature measurement according to the method of FIG. 4 yields readings with greater accuracy than those obtained from sensor element impedance. This range of temperatures may be a first, lower range of temperatures including engine cold start temperatures where oxygen sensor temperature is below 550° C., for example. Similarly, oxygen sensor temperature may be preferentially determined based on sensor element impedance for a range of temperatures in which it is known that impedance temperature measurement yields readings with greater accuracy than those obtained from heater resistance. This range of temperatures may be a second, higher range of temperatures including temperatures extending from when oxygen sensor temperature is above 550° C.

Since the resistance of heater 207 correlates to the temperature of oxygen sensor 126 below, at, and above the threshold temperature, the heater resistance may be used to persistently determine the temperature of the oxygen sensor throughout the duration of sensor operation. If the resistance of heater 207 indicates a temperature at or below the threshold temperature, this resistance alone may be used to determine the temperature of oxygen sensor 126. If, conversely, the resistance of heater 207 indicates a temperature above the threshold temperature, an impedance measurement of an oxygen sensor element may be subsequently performed, with both the measured resistance and impedance being used to determine the temperature of oxygen sensor 126 as described above.

Thus, the system of FIGS. 1 and 2 provides for a system, comprising: an engine; an oxygen sensor; an alternator; and a controller including executable instructions stored in non-transitory memory to apply a first field current to the alternator during a first cold start of the engine to generate a first voltage, apply a second field current to the alternator during a second cold start of the engine to generate a second voltage, the second voltage greater than the first voltage, the first voltage based on a low oxygen sensor heater resistance, the second voltage based on an estimated oxygen sensor heater resistance. The system further comprises additional instructions to determine the estimated oxygen sensor heater resistance via integrating the first voltage during the first cold start of the engine. The system includes where the second voltage is greater than the first voltage when the estimated oxygen sensor heater resistance is greater than the low oxygen sensor heater resistance. The system further comprises additional instructions to sense a pumping current of the oxygen sensor via the controller. The system further comprises additional instructions to cease integrating the first voltage in response to sensing the pumping current of the oxygen sensor.

Referring now to FIG. 3, plots of a prophetic engine operating sequence according to the method of FIG. 4 and the system of FIGS. 1 and 2 is shown. The plots are aligned in time and occur at a same time. The vertical lines at t0-t12 show events at particular times of interest. The // marks along the horizontal axis represent a break in time and the break in time is sufficient for the engine to reach ambient temperature so that each engine start is a cold engine start (e.g., the engine is started below a temperature of 20° C.).

The first plot from the top of FIG. 3 is a plot of engine operating state versus time. The engine is stopped (e.g., not combusting fuel and not rotating) when trace 302 is at a lower level near the horizontal axis. The engine is started and running (e.g., rotating and combusting fuel) when trace 302 is at a higher level near the vertical axis arrow. The horizontal axis represents time and time increases from the left side of the plot to the right side of the plot. Trace 302 represents the engine operating state.

The second plot from the top of FIG. 3 is a plot of oxygen sensor output voltage versus time. The oxygen sensor output voltage indicates that pumping current in the oxygen sensor is detected when the oxygen sensor output level is above the horizontal axis. Note that in some examples a pumping current may be indicated by a decrease in output voltage of the oxygen sensor, or alternatively, trace 304 may represent pumping cell current. The horizontal axis represents time and time increases from the left side of the plot to the right side of the plot. Trace 304 represents the oxygen sensor output voltage.

The third plot from the top of FIG. 3 is a plot of oxygen sensor heater input voltage versus time. The oxygen sensor heater input voltage increases in the direction of the vertical axis arrow. The horizontal axis represents time and time increases from the left side of the plot to the right side of the plot. Trace 306 represents oxygen sensor heater input voltage.

The fourth plot from the top of FIG. 3 is a plot of integrated oxygen sensor heater input voltage versus time. The integrated oxygen sensor heater input voltage increases in the direction of the vertical axis arrow. The horizontal axis represents time and time increases from the left side of the plot to the right side of the plot. Trace 308 represents integrated oxygen sensor heater input voltage.

At time to, the engine is stopped (e.g., not rotating and not combusting fuel) as indicated by trace 302 being at a low level. There is no output from the oxygen sensor and no voltage is applied to the oxygen sensor heater. The integrated oxygen sensor heater input voltage is zero.

At time t1, the engine is started in response to a request to start the engine (not shown) and a voltage is applied to the oxygen sensor heater. The voltage is applied at a middle upper level in response to the engine being cold started a first time after the engine is manufactured. At this juncture in time, the oxygen sensor's heater resistance has not been estimated so that a lower voltage is applied to the oxygen sensor heater. The lower voltage is applied so that a threshold level of electrical power delivered to the oxygen sensor is not exceeded. This may prevent oxygen sensor degradation at a time when the oxygen sensor heater resistance is unknown. The lower voltage level is applied to the oxygen sensor based on an initial assumption that the oxygen sensor heater resistance is low. By applying a lower voltage level to the oxygen sensor heater, it may be possible to prevent the oxygen sensor from being exposed to high electrical power levels that may degrade the oxygen sensor if the oxygen sensor's resistance is indeed a low value. Integration of the oxygen sensor input voltage begins and there is no output from the oxygen sensor.

Between time t1 and time t2, the engine continues to operate and oxygen sensor output is zero. The oxygen sensor heater input voltage remains at its previous level and the integrated oxygen sensor heater input voltage value continuously increases.

At time t2, oxygen sensor pumping current is indicated while the engine continues to run. Integration of the oxygen sensor input voltage is discontinued in response to the indication of oxygen sensor output because this indicates that the oxygen sensor has reached about 550° C. The oxygen sensor heater input voltage is increased after time t2 based on the impedance of the sensor element to provide a desired oxygen sensor temperature. The resistance of the oxygen sensor heater is estimated based on the integrated oxygen sensor heater input voltage as described in the method of FIG. 4. The engine may enter closed-loop air-fuel control at time t2 since the oxygen sensor is outputting useful data.

At time t10, the engine is stopped (e.g., not rotating and not combusting fuel) as indicated by trace 302 being at a low level. There is no output from the oxygen sensor and no voltage is applied to the oxygen sensor heater. The integrated oxygen sensor heater input voltage is zero.

At time t11, the engine is started in response to a request to start the engine (not shown) and a voltage is applied to the oxygen sensor heater. The voltage is applied at an upper level in response to an oxygen sensor heater resistance estimate that is based on the integrated oxygen sensor heater input voltage as determined between time t1 and time t2. In this example, it is estimated that the oxygen sensor's heater resistance is greater than the initial resistance used to determine the voltage that was applied to the oxygen sensor heater at time t1. Therefore, a higher voltage is applied to the oxygen sensor heater so that the oxygen sensor may become activated sooner. Further, the voltage applied to the oxygen sensor at time t11 is based on an amount of power that the oxygen sensor heater may consume without a significant risk of oxygen sensor degradation. Integration of the voltage that is applied to the oxygen sensor heater begins and the oxygen sensor does not provide an output signal indicating the presence of oxygen sensor pumping current.

Between time t11 and time t12, the engine continues to operate and oxygen sensor output is zero. The oxygen sensor heater input voltage remains at its previous level and the integrated oxygen sensor heater input voltage value continuously increases.

At time t12, oxygen sensor pumping current is indicated while the engine continues to run. Integration of the oxygen sensor input voltage is discontinued in response to the indication of oxygen sensor output because this indicates that the oxygen sensor has reached about 550° C. The oxygen sensor heater input voltage is increased after time t12 based on the impedance of the sensor element to provide a desired oxygen sensor temperature. The resistance of the oxygen sensor heater is estimated based on the integrated oxygen sensor heater input voltage as described in the method of FIG. 4. Because a higher voltage is applied to the oxygen sensor heater, the amount of time between t11 and t12 is much shorter than the amount of time between time t1 and time t2. This may allow the engine to enter closed-loop air-fuel control sooner (e.g., at time t12).

In this way, resistance of an oxygen sensor heater may be estimated at lower temperatures. Further, the estimate of oxygen sensor heater resistance may be applied during a subsequent engine cold start so that the engine may enter close-loop air-fuel ratio control sooner, thereby reducing engine emissions.

Referring now to FIG. 4, a flow chart of a method for operating an engine and oxygen sensor to reduce an amount of time between engine starting and closed-loop engine air-fuel ratio control is shown. The method of FIG. 4 may be incorporated into and may cooperate with the system of FIGS. 1 and 2. Further, at least portions of the method of FIG. 4 may be incorporated as executable instructions stored in non-transitory memory while other portions of the method may be performed via a controller transforming operating states of devices and actuators in the physical world.

At 402, method 400 determines vehicle operating conditions. Vehicle operating conditions may include but are not limited to vehicle speed, engine speed, engine temperature, electric energy storage device state of charge (SOC), barometric pressure, and accelerator pedal position, and air charge in each engine cylinder. Method 400 proceeds to 404.

At 404, method 400 judges if a cold engine start is requested (e.g., an engine start below a threshold temperature, for example 20° C., is requested). The engine cold start may be requested via a human or autonomous driver. In one example, method 400 may judge that a cold engine start is requested if engine temperature is less than a threshold temperature and the engine has not been combusting fuel for longer than a threshold amount of time. If method 400 judges that engine cold start is requested, the answer is yes and method 400 proceeds to 406. Otherwise, the answer is no and method 400 proceeds to 430.

At 430, method 400 judges if oxygen sensor heater resistance has been previously estimated. Method 400 may judge that the oxygen sensor heater resistance has been previously estimated based on a value of a variable in controller memory. If method 400 judges that oxygen sensor resistance has been previously estimated, the answer is yes and method 400 proceeds to 432. Otherwise, the answer is no and method 400 proceeds to 434.

At 434, method 400 operates the engine and the oxygen sensor based on an assumption that the oxygen sensor heater resistance is a predetermined lower resistance amount. However, if the oxygen sensor is at operating temperature (e.g., above 550° C.), then the oxygen sensor may be supplied with a heater voltage that is based on oxygen sensor temperature that is estimated from the oxygen sensor sensing element impedance. For example, if the engine is warm and started above a threshold engine temperature, but the oxygen sensor temperature is less than a threshold temperature, then the resistance of the oxygen sensor may be estimated to be, or assumed to be, a lower resistance amount X. If it is determined that the oxygen sensor may receive up to Y watts of power, then the voltage that is applied to the oxygen sensor heater may be adjusted to the voltage $V=\sqrt{Y \cdot X}$, where V is the voltage that is applied to the oxygen sensor heater. The lower resistance amount X may be determined via measuring resistance levels of a group of oxygen sensors at temperatures that are less than a threshold temperature (e.g., 20° C.). The engine may be operated to output torque according to the accelerator pedal position and vehicle speed. In this way, the voltage that is supplied to the oxygen sensor heater may be based on a lower predetermined oxygen sensor heater resistance so that the amount of electric power that is supplied to the oxygen sensor heater may not degrade the oxygen sensor. Further, the engine may be closed-loop fuel controlled once the oxygen sensor's pumping current is detected. For example, opening times for the engine's fuel injectors may be adjusted responsive to a desired engine air-fuel ratio and output of the oxygen sensor. Method 400 proceeds to exit.

At 432, method 400 operates the engine and the oxygen sensor based on a previously estimated oxygen sensor heater resistance. However, if the oxygen sensor is at operating temperature (e.g., above 550° C.), then the oxygen sensor may be supplied with a heater voltage that is based on oxygen sensor temperature that is estimated from the oxygen sensor sensing element impedance. For example, if the engine is warm and started above a threshold engine temperature, but the oxygen sensor temperature is less than a threshold temperature, then the resistance of the oxygen sensor may be an estimated resistance determined at 414. The estimated oxygen sensor resistance may be a value R. If it is determined that the oxygen sensor may receive up to Y watts of power, then the voltage that is applied to the oxygen sensor heater may be adjusted to a voltage $V=\sqrt{Y \cdot R}$, where V is the voltage that is applied to the oxygen sensor heater. The engine may be operated to output torque according to the accelerator pedal position and vehicle speed. In this way, the voltage that is supplied to the oxygen sensor heater may be based on an estimated oxygen sensor heater resistance that was determined via integrating a voltage that was applied to the oxygen sensor heater. Further, the engine may be closed-loop fuel controlled once the oxygen sensor's pumping current is detected. For example, opening times for the engine's fuel injectors may be adjusted responsive to a desired engine air-fuel ratio and output of the oxygen sensor. Method 400 proceeds to exit.

At 406, method 400 judges if it is desired to estimate the oxygen sensor heater resistance. In one example, the oxygen sensor heater resistance is initially estimated (e.g., estimated for a first time since engine manufacture) during a first cold start of the engine. Further, method 400 may judge that it is desirable to estimate oxygen sensor heater resistance according to a predetermined schedule (e.g., every cold engine start until a repeatable resistance level is determined and at every 5000 kilometers of vehicle distance traveled thereafter). If method 400 judges that it is desirable to estimate oxygen sensor resistance, then the answer is yes and method 400 proceeds to 408. Otherwise, the answer is no and method 400 proceeds to 420.

At 420, method 400 operates the engine and the oxygen sensor based on a present value of oxygen sensor heater resistance. The present value may be a predetermined lower oxygen sensor heater resistance if the oxygen sensor heater resistance has not been estimated, or it may be the estimated oxygen sensor heater resistance as determined at 414. For example, the voltage applied to the oxygen sensor heater may be adjusted to a level based on the equation: $v=\sqrt{Y \cdot R}$, where V is the voltage applied to the oxygen sensor heater, Y is the desired amount of power to be delivered to the oxygen sensor heater, and R is the oxygen sensor heater resistance value (e.g., the predetermined lower value or the estimated value from 414). In this way, the voltage that is supplied to the oxygen sensor heater may be based on an estimated oxygen sensor heater resistance that was determined via integrating a voltage that was applied to the oxygen sensor heater or the predetermined lower oxygen sensor heater resistance value. The engine may be started with the voltage being applied to the oxygen sensor heater. Further, the engine may be closed-loop fuel controlled once the oxygen sensor's pumping current is detected. For example, opening times for the engine's fuel injectors may be adjusted responsive to a desired engine air-fuel ratio and output of the oxygen sensor. Method 400 proceeds to exit.

At 408, method 400 operates the engine and the oxygen sensor based on a present value of oxygen sensor heater resistance. The present value may be a predetermined lower oxygen sensor heater resistance if the oxygen sensor heater resistance has not been estimated, or it may be the estimated oxygen sensor heater resistance as determined at 414. For example, the voltage applied to the oxygen sensor heater may be adjusted to a level based on the equation: $v=\sqrt{Y \cdot R}$, where V is the voltage applied to the oxygen sensor heater, Y is the desired amount of power to be delivered to the oxygen sensor heater, and R is the oxygen sensor heater resistance value (e.g., the predetermined lower value or the estimated value from 414). In this way, the voltage that is supplied to the oxygen sensor heater may be based on an estimated oxygen sensor heater resistance that was determined via integrating a voltage that was applied to the oxygen sensor heater or the predetermined lower oxygen sensor heater resistance value. The predetermined lower oxygen sensor heater resistance value is applied the first time the engine is cold started after manufacture of the engine. The engine may be started with the voltage being applied to the oxygen sensor heater during engine cranking and run-up. Further, the engine may be closed-loop fuel controlled once the oxygen sensor's pumping current is detected. For example, opening times for the engine's fuel injectors may be adjusted responsive to a desired engine air-fuel ratio and output of the oxygen sensor. Method 400 proceeds to 410.

At 410, method 400 integrates the value of the voltage that is applied to the oxygen sensor heater. The integration begins when voltage is first applied to the oxygen sensor heater after a time when no voltage is applied to the oxygen sensor heater. Method 400 proceeds to 412.

At 412, method 400 judges if oxygen sensor pumping current is detected or indicated by oxygen sensor output voltage or an oxygen sensor pumping current level. If oxygen sensor pumping current is indicated, the answer is yes and method 400 proceeds to 414. Otherwise, the answer is no and method 400 returns to 410.

At 414, method 400 ceases integrating the voltage that is applied to the oxygen sensor heater. Further, method 400 estimates the oxygen sensor heater resistance via the following equation:

$$R = \frac{\int V^2(t)dt}{E_{550}}$$

where R is the estimated oxygen sensor heater resistance, V is the voltage level that is applied to the oxygen sensor heater, and $E_{550}$ is an amount of energy to raise the oxygen sensor temperature to 550° C. The variable $E_{550}$ may be empirically determined for various initial oxygen sensor temperatures and the value of $E_{550}$ for a particular engine starting temperature may be determined via referencing a table or function of empirically determined energy amounts based on engine temperature. The values in the table or function may be determined via measuring current and voltage applied to an oxygen sensor heater and determining the amount of power input into the oxygen sensor heater that allows the oxygen sensor to reach 550° C. In one example, E550 is determined from the nominal resistance of a nominal oxygen sensor as the oxygen sensor is heated over a standardized temperature range (e.g., 20° C. to 550° C.) using a constant reference voltage. The reference voltage may be determined from the lowest heater resistance over the entire range of heater resistance values. For example, if the nominal resistance of the oxygen sensor heater is 4 ohms, and the range of resistance values for a group of nominal sensors is from 3 ohms to 5 ohms, then the reference voltage is the maximum allowable voltage for the 3 ohm resistance heater. Using this reference voltage, a sensor with the nominal heater resistance of 4 ohms would be used to determine E550. This value for E550 may then be used to determine the resistance value R for other unknown heater resistances by measuring the time it takes for the sensor to heat up over the standard temperature range using the constant reference voltage. Method 400 proceeds to 416 after estimating the oxygen sensor heater resistance.

At 416, method 400 operates the engine and the oxygen sensor based on the estimated oxygen sensor heater resistance. For example, the voltage applied to the oxygen sensor heater may be adjusted to a level based on the equation: $v=\sqrt{Y \cdot R}$, where V is the voltage applied to the oxygen sensor heater, Y is the desired amount of power to be delivered to the oxygen sensor heater, and R is the estimated oxygen sensor heater resistance value. In this way, the voltage that is supplied to the oxygen sensor heater may be based on an estimated oxygen sensor heater resistance that was determined via integrating a voltage that was applied to the oxygen sensor heater or the predetermined lower oxygen sensor heater resistance value. The engine may be subsequently started with a voltage being applied to the oxygen sensor heater that is based on the estimated oxygen sensor heater resistance. Further, the engine may be closed-loop fuel controlled once the oxygen sensor's pumping current is detected via the controller. For example, opening times for the engine's fuel injectors may be adjusted responsive to a desired engine air-fuel ratio and output of the oxygen sensor. Method 400 proceeds to exit.

In this way, a resistance of an oxygen sensor may be determined so that a voltage that is based on the estimated oxygen sensor heater resistance may be applied to the oxygen sensor to reduce an amount of time it takes for the engine to enter closed-loop fuel control during and after a cold engine start. The voltage that is applied to the oxygen sensor heater may further be based on a desired amount of electrical power to deliver to the oxygen sensor heater. The desired amount of power may be empirically determined via supplying various power levels to oxygen sensor heaters and monitoring the oxygen sensors for signs of degradation.

Thus, the method of FIG. 4 provides for an oxygen sensor operating method, comprising: supplying a voltage to an oxygen sensor heater during a cold engine start via a controller; integrating the voltage; and adjusting the voltage applied to the oxygen sensor heater applied during a subsequent cold engine start via the controller responsive to the integrated voltage. The method includes where the voltage is based on an initial low estimate of resistance of the oxygen sensor heater. The method further comprises adjusting the voltage applied to the oxygen sensor heater via dividing the integrated voltage via a predetermined amount of energy. The method includes where the voltage is adjusted via increasing a field current of an alternator. The method includes where adjusting the voltage includes increasing the voltage applied to the oxygen sensor. The method further comprises sensing an output of the oxygen sensor via the controller. The method further comprises adjusting an engine air-fuel ratio responsive to the output of the oxygen sensor. The method includes where the oxygen sensor is positioned in an engine exhaust system upstream of a catalyst.

The method of FIG. 4 also provides for an oxygen sensor operating method, comprising: supplying a voltage to an oxygen sensor heater during a cold engine start via a controller; integrating the voltage beginning at a time when the voltage is applied to the oxygen sensor heater and ending at a time when a pumping current of an oxygen sensor is detected; and adjusting the voltage applied to the oxygen sensor heater applied during a subsequent cold engine start via the controller responsive to the integrated voltage. The method further comprises adjusting an engine air-fuel ratio responsive to an output of the oxygen sensor. The method includes where adjusting the voltage applied to the oxygen sensor heater applied during a subsequent cold engine start includes adjusting the voltage applied to the oxygen sensor heater applied during a subsequent cold engine start via increasing alternator field current. The method further comprises estimating an oxygen sensor heater resistance via the integrated voltage. The method includes where adjusting the voltage applied to the oxygen sensor heater applied during the subsequent cold engine start includes increasing the voltage applied to the oxygen sensor heater in response to the estimated oxygen sensor heater resistance increasing. The method further comprises storing the estimated oxygen sensor heater resistance to controller memory. The method includes where the voltage supplied to the oxygen sensor heater during the cold engine start is based on a low resistance oxygen sensor heater.

In another representation, the method of FIG. 4 provides for an engine operating method, comprising: estimating an oxygen sensor heater resistance via dividing an integrated voltage by a predetermined energy amount for heating an oxygen sensor to a predetermined temperature; and supplying a voltage to an oxygen sensor heater based on the estimated oxygen sensor heater resistance. In one example, the integration is performed from a time when a voltage is first applied to the oxygen sensor heater to a time when pumping current within the oxygen sensor is indicated. The oxygen sensor heater resistance may be determined at predetermined intervals.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, at least a portion of the described actions, operations and/or functions may graphically represent code to be programmed into non-transitory memory of the computer readable storage medium in the control system. The control actions may also transform the operating state of one or more sensors or actuators in the physical world when the described actions are carried out by executing the instructions in a system including the various engine hardware components in combination with one or more controllers.

This concludes the description. The reading of it by those skilled in the art would bring to mind many alterations and modifications without departing from the spirit and the scope of the description. For example, single cylinder, I3, I4, I5, V6, V8, V10, and V12 engines operating in natural gas, gasoline, diesel, or alternative fuel configurations could use the present description to advantage.

The invention claimed is:

1. A system, comprising:
   an engine;
   an oxygen sensor;
   an alternator; and
   a controller including executable instructions stored in non-transitory memory to apply a first field current to the alternator during a first cold start of the engine to generate a first voltage, apply a second field current to the alternator during a second cold start of the engine to generate a second voltage, the second voltage greater than the first voltage, the first voltage based on a low oxygen sensor heater resistance, the second voltage based on an estimated oxygen sensor heater resistance.

2. The system of claim 1, further comprising additional instructions to determine the estimated oxygen sensor heater resistance via integrating the first voltage during the first cold start of the engine.

3. The system of claim 2, where the second voltage is greater than the first voltage when the estimated oxygen sensor heater resistance is greater than the low oxygen sensor heater resistance.

4. The system of claim 1, further comprising additional instructions to sense a pumping current of the oxygen sensor via the controller.

5. The system of claim 4, further comprising additional instructions to cease integrating the first voltage in response to sensing the pumping current of the oxygen sensor.

6. An oxygen sensor operating method, comprising:
supplying a voltage to an oxygen sensor heater during a cold engine start via a controller;
integrating the voltage; and
adjusting the voltage applied to the oxygen sensor heater applied during a subsequent cold engine start via the controller responsive to integrating the voltage.

7. The method of claim 6, where the voltage is based on an initial low estimate of resistance of the oxygen sensor heater.

8. The method of claim 7, further comprising adjusting the voltage applied to the oxygen sensor heater via dividing the integrated voltage via a predetermined amount of energy.

9. The method of claim 6, where the voltage is adjusted via increasing a field current of an alternator.

10. The method of claim 9, where adjusting the voltage includes increasing the voltage applied to the oxygen sensor.

11. The method of claim 6, further comprising sensing an output of the oxygen sensor via the controller.

12. The method of claim 11, further comprising adjusting an engine air-fuel ratio responsive to the output of the oxygen sensor.

13. The method of claim 12, where the oxygen sensor is positioned in an engine exhaust system upstream of a catalyst.

14. An oxygen sensor operating method, comprising:
supplying a voltage to an oxygen sensor heater during a cold engine start via a controller;
integrating the voltage beginning at a time when the voltage is applied to the oxygen sensor heater and ending at a time when a pumping current of an oxygen sensor is detected; and
adjusting the voltage applied to the oxygen sensor heater applied during a subsequent cold engine start via the controller responsive to integrating the voltage.

15. The method of claim 14, further comprising adjusting an engine air-fuel ratio responsive to an output of the oxygen sensor.

16. The method of claim 15, where adjusting the voltage applied to the oxygen sensor heater applied during a subsequent cold engine start includes adjusting the voltage applied to the oxygen sensor heater applied during a subsequent cold engine start via increasing alternator field current.

17. The method of claim 14, further comprising estimating an oxygen sensor heater resistance via the integrated voltage.

18. The method of claim 17, where adjusting the voltage applied to the oxygen sensor heater applied during the subsequent cold engine start includes increasing the voltage applied to the oxygen sensor heater in response to the estimated oxygen sensor heater resistance increasing.

19. The method of claim 17, further comprising storing the estimated oxygen sensor heater resistance to controller memory.

20. The method of claim 19, where the voltage supplied to the oxygen sensor heater during the cold engine start is based on a low resistance oxygen sensor heater.

* * * * *